United States Patent
Hübner et al.

(10) Patent No.: US 9,873,646 B2
(45) Date of Patent: Jan. 23, 2018

(54) PROCESS FOR PREPARING CYCLOHEXANE FROM BENZENE AND METHYLCYCLOPENTANE WITH UPSTREAM BENZENE HYDROGENATION

(71) Applicant: BASF SE, Ludwigshafen (DE)

(72) Inventors: Michael Hübner, Weinheim (DE); Lukas Schulz, Mannheim (DE); Pawel Czajka, Mannheim (DE); Oliver Christian Gobin, München (DE); Nicole Holub, Mannheim (DE); Daniel Pfeiffer, Neustadt (DE); Andreas Weickgenannt, Mannheim (DE); Marta Porta Garcia, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/305,111

(22) PCT Filed: Apr. 20, 2015

(86) PCT No.: PCT/EP2015/058526
§ 371 (c)(1),
(2) Date: Oct. 19, 2016

(87) PCT Pub. No.: WO2015/162097
PCT Pub. Date: Oct. 29, 2015

(65) Prior Publication Data
US 2017/0121240 A1    May 4, 2017

(30) Foreign Application Priority Data

Apr. 22, 2014  (EP) ................................... 14165503

(51) Int. Cl.
*C07C 5/10*    (2006.01)
*C07C 5/27*    (2006.01)
(Continued)

(52) U.S. Cl.
CPC .................. *C07C 5/03* (2013.01); *C07C 5/31* (2013.01); *C07C 7/04* (2013.01); *C07C 2527/126* (2013.01)

(58) Field of Classification Search
CPC ................ C07C 5/10; C07C 5/27; C07C 5/31
(Continued)

(56) References Cited

U.S. PATENT DOCUMENTS 2,846,485 A    8/1958  Meason et al.
3,233,001 A    2/1966  Merryfield et al.
(Continued)

FOREIGN PATENT DOCUMENTS

EP    1127601 A2    8/2001
EP    1403236 A1    3/2004
(Continued)

OTHER PUBLICATIONS

International Search Report for PCT/EP2015/058526 dated Jun. 25, 2015.
(Continued)

*Primary Examiner* — Thuan D Dang
(74) *Attorney, Agent, or Firm* — Drinker Biddle & Reath LLP (57) ABSTRACT

The present invention relates to a process for preparing cyclohexane from methylcyclopentane (MCP) and benzene. In the context of the present invention, MCP and benzene are constituents of a hydrocarbon mixture (HM1) additionally comprising dimethylpentanes (DMP), possibly cyclohexane and possibly at least one compound (low boiler) selected from acyclic $C_5$-$C_6$-alkanes and cyclopentane. First of all, benzene is converted in a hydrogenation step to cyclohexane (that present in the hydrocarbon mixture (HM2)), while MCP is isomerized in the presence of a catalyst, preferably of an acidic ionic liquid, to cyclohexane. After the hydro-
(Continued)

genation but prior to the isomerization the dimethylpentanes (DMP) are removed, with initial removal of the cyclohexane present in the hydrocarbon mixture (HM2) together with DMP. This cyclohexane already present prior to the isomerization can be separated again from DMP in a downstream rectification step and isolated and/or recycled into the process for cyclohexane preparation. Between the DMP removal and MCP isomerization—if low boilers are present in the hydrocarbon mixture (HM1)—low boilers are, optionally removed. After the isomerization, the cyclohexane is isolated, optionally with return of unisomerized MCP and optionally of low boilers. Preferably, cyclohexane and/or low boilers are present in the hydrocarbon mixture (HM1), and so a low boiler removal is preferably conducted between the DMP removal from isomerization. It is additionally preferable that the removal of the cyclohexane from DMP is additionally conducted, meaning that the cyclohexane component which arises in the benzene hydrogenation and may be present in the starting mixture (HM1) is isolated and hence recovered.

29 Claims, 2 Drawing Sheets (51) Int. Cl.
  *C07C 5/31* (2006.01)
  *C07C 5/03* (2006.01)
  *C07C 7/04* (2006.01)
(58) Field of Classification Search
  USPC .......................................... 585/317, 318, 379
  See application file for complete search history.

(56) References Cited

U.S. PATENT DOCUMENTS

| | | | |
|---|---|---|---|
| 3,309,411 A | 3/1967 | Waldby et al. | |
| 3,311,667 A | 3/1967 | Cabbage | |
| 3,406,217 A | 10/1968 | Davison et al. | |
| 4,053,369 A | 10/1977 | Cines | |
| 4,955,468 A | 9/1990 | Lee | |
| 6,503,465 B1 | 1/2003 | Lin et al. | |
| 8,092,655 B2 | 1/2012 | Burst et al. | |
| 8,410,327 B2 | 4/2013 | Tschirschwitz et al. | |
| 9,095,789 B2 | 8/2015 | Pfeiffer et al. | |
| 9,409,839 B2 | 8/2016 | Pfeiffer et al. | |
| 2003/0109767 A1 | 6/2003 | Vasina et al. | |
| 2005/0082201 A1 | 4/2005 | Groten et al. | |
| 2011/0137098 A1 | 6/2011 | Tschirschwitz et al. | |
| 2014/0014596 A1 | 1/2014 | Pfeiffer et al. | |
| 2014/0018588 A1 | 1/2014 | Spuhl et al. | |
| 2014/0018590 A1 | 1/2014 | Tschirschwitz et al. | |
| 2014/0018591 A1 | 1/2014 | Tschirschwitz et al. | |
| 2014/0018595 A1 | 1/2014 | Spuhl et al. | |
| 2014/0018597 A1 | 1/2014 | Pfeiffer et al. | |
| 2014/0024875 A1 | 1/2014 | Spuhl et al. | |
| 2014/0114099 A1 | 4/2014 | Tschirschwitz et al. | |
| 2014/0114100 A1 | 4/2014 | Tschirschwitz et al. | |
| 2014/0114103 A1 | 4/2014 | Schmitt et al. | |
| 2014/0128648 A1 | 5/2014 | Prochazka et al. | |
| 2014/0257003 A1 | 9/2014 | Tschirschwitz et al. | |
| 2014/0257007 A1 | 9/2014 | Bitterlich et al. | |
| 2015/0166455 A1 | 6/2015 | Hammon et al. | |

FOREIGN PATENT DOCUMENTS

| | | | |
|---|---|---|---|
| EP | 1992673 A1 | 11/2008 | |
| EP | 1995297 A1 | 11/2008 | |
| JP | S48-102802 A | 12/1973 | |
| JP | S61-263932 A | 11/1986 | |
| JP | H03-287548 A | 12/1991 | |
| JP | H07-278569 A | 10/1995 | |
| JP | H09-188633 A | 7/1997 | |
| JP | H10-036295 A | 2/1998 | |
| WO | WO-02/22528 A1 | 3/2002 | |
| WO | WO-2010/027987 A2 | 3/2010 | |
| WO | WO-2011/069929 A1 | 6/2011 | |
| WO | WO-2011/069957 A1 | 6/2011 | |
| WO | WO-2015/082388 A1 | 6/2015 | |

OTHER PUBLICATIONS

Fair, J. R., "Distillation" in Kirk-Othmer Encyclopedia of Chemical Technology, Fifth Edition, vol. 8, pp. 739-785, 2004.
International Preliminary Report on Patentability for PCT/EP2015/058526 dated Oct. 25, 2016 with English Translation Attached.
Office Action Issued in Japanese Application No. 2016-563957 Dated Jul. 19, 2017 with English Translation Attached.

PROCESS FOR PREPARING CYCLOHEXANE FROM BENZENE AND METHYLCYCLOPENTANE WITH UPSTREAM BENZENE HYDROGENATION

RELATED APPLICATIONS

This application is a national stage application (under 35 U.S.C. §371) of PCT/EP2015/058526, filed Apr. 20, 2015, which claims benefit of European Application No. 14165501.5, filed Apr. 22, 2014.

The present invention relates to a process for preparing cyclohexane from methylcyclopentane (MCP) and benzene. In the context of the present invention, MCP and benzene are constituents of a hydrocarbon mixture (HM1) additionally comprising dimethylpentanes (DMP), possibly cyclohexane and possibly at least one compound (low boiler) selected from acyclic $C_5$-$C_6$-alkanes and cyclopentane. First of all, benzene is converted in a hydrogenation step to cyclohexane (that present in the hydrocarbon mixture (HM2)), while MCP is isomerized in the presence of a catalyst, preferably of an acidic ionic liquid, to cyclohexane. After the hydrogenation, but prior to the isomerisation, the dimethylpentanes (DMP) are removed, with initial removal of the cyclohexane present in the hydrocarbon mixture (HM2) together with DMP. This cyclohexane already present prior to the isomerization can be separated again from DMP in a downstream rectification step and isolated and/or recycled into the process for cyclohexane preparation. Between the DMP removal and MCP isomerization—if low boilers are present in the hydrocarbon mixture (HM1)—low boilers are optionally removed. After the isomerization, the cyclohexane is isolated, optionally with return of unisomerized MCP and optionally of low boilers. Preferably, cyclohexane and/or low boilers are present in the hydrocarbon mixture (HM1), and so a low boiler removal is preferably conducted between the DMP removal from isomerization. It is additionally preferable that the removal of the cyclohexane from DMP is additionally conducted, meaning that the cyclohexane component which arises in the benzene hydrogenation and may be present in the starting mixture (HM1) is isolated and hence recovered.

Cyclohexane is an important product of value in the chemical industry, which is preferably prepared by hydrogenation of benzene provided in substantially pure form. However, the problem arises that benzene is a scarce product and therefore hydrogenation to cyclohexane competes with other uses, for example the preparation of styrene. There is therefore an incentive to find a preparation process for cyclohexane which proceeds from a feedstock other than pure benzene.

It is additionally known that cyclohexane can be prepared not only by hydrogenation of benzene but also by isomerization of MCP. The catalysts used for such an isomerization are preferably acidic catalysts in the form of a Lewis or Brønsted acid, for example Friedel-Crafts catalysts or else acidic ionic liquids.

The benzene and MCP reactants usable for cyclohexane preparation are frequently constituents of hydrocarbon mixtures. The specific composition of the hydrocarbon mixtures may vary significantly; they frequently also comprise dimethylpentanes (DMP). In addition, these hydrocarbon mixtures may also already comprise the actual cyclohexane target product.

In order, however, to obtain a pure target product, i.e. on-spec cyclohexane, the cyclohexane has to be separated from all other components still present in the hydrocarbon mixture after the hydrogenation or isomerization, thus including the DMP present in the starting mixture. However, the separation of the DMP from cyclohexane, the actual process product, is technically quite demanding and complex, especially where the 2,4-dimethylpentane (2,4-DMP) isomer of DMP is concerned. The standard boiling point of 2,4-DMP at 80.52° C. is very similar to the standard boiling point of cyclohexane (80.78° C.), whereas the standard boiling points of the other DMP isomers have a greater separation from cyclohexane (2,3-DMP has, for example, a standard boiling point of 89.88° C.).

US-A 2003/0109767 discloses a process for isomerizing $C_5$-$C_8$ paraffin hydrocarbons (paraffins) in the presence of an ionic liquid as a catalyst. The ionic liquid comprises, as cations, nitrogen-containing heterocycles or nitrogen-containing aliphatics; the corresponding anions are derived from metal halides. The paraffins to be isomerized are linear alkanes such as n-hexane or n-octane and monosubstituted alkanes such as 3-methylhexane or mixtures thereof. The process described in US-A 2003/0109767 is intended to prepare paraffins having a relatively high degree of branching. In contrast, cyclohexane, for example, has a lower degree of branching compared to MCP. Moreover, US-A 2003/0109767 does not make any statements to the effect that any aromatics present in the starting mixture are hydrogenated prior to the isomerization. US-A 2003/0109767 additionally does not state that the material used for isomerization may also comprise DMP. Consequently, this document also does not contain any statements as to the point at which DMP is removed from cyclohexane, or that this removal is problematic.

In the isomerization process described in EP-A 1 403 236, the intention is likewise to obtain a relatively high degree of branching in the paraffins (hydrocarbons) to be isomerized in the presence of an ionic liquid. The isomerization process is additionally performed in the presence of cyclic hydrocarbons as additives and in a reaction medium, the cyclic hydrocarbons comprising a tertiary carbon atom as a structural unit, or being converted by the reaction medium to a corresponding compound having such a structural unit. Preference is given to using methylcyclohexane or dimethylcyclopentane as such cyclic hydrocarbon additives. The paraffins to be isomerized are linear alkanes such as n-butane or n-octane, and monomethyl-substituted alkanes such as 2-methylhexane. The ionic liquids are preferably based on nitrogen-containing heterocycles or nitrogen-containing aliphatics as cations, and on inorganic anions such as haloaluminates. EP-A 1 403 236 likewise does not contain any statements that any aromatics present in the starting mixture are hydrogenated prior to the isomerization. The same also applies to any presence of DMP in the starting mixture.

US-A2005/0082201 discloses a process for preparing gasoline with a low benzene content, wherein, in a first process step, a hydrocarbon mixture comprising benzene, olefins and sulfur compounds such as thiophenes is first fed into a rectification column, from which the low-boiling compounds are removed via the top, a benzene-containing fraction via a side draw and the high boilers from the column bottom. In a second process stage, the fraction obtained from the side draw is hydrogenated in the presence of a hydrogenation catalyst, converting benzene to cyclohexane and the thiophenes to hydrogen sulfide. The cyclohexane-containing mixture obtained in the second process stage is suitable for preparation of gasoline having a low benzene content. No isolation of the cyclohexane present therein, or any isomerization in general, for example of MCP to cyclohexane, is disclosed in US-A2005/0082201. The same also applies to any presence of DMP in the starting mixture.

WO 2010/027987 relates to a further process for reducing the concentration of benzene in a hydrocarbonaceous mixture. In a first separation stage, a benzene-containing fraction comprising benzene and other $C_6$ hydrocarbons is separated from a high boiler fraction comprising carbons having seven or more carbon atoms. The benzene-containing fraction is subsequently hydrogenated to obtain a hydrocarbon fraction having a reduced benzene content. The hydrogenation of benzene forms cyclohexane. WO 2010/027987 also does not contain any pointers that cyclohexane can be isolated from the mixture obtained in the hydrogenation; instead, this process product too is to be used for gasoline production. This document likewise does not disclose isomerization of MCP to cyclohexane or the presence of DMP in the hydrocarbon starting mixture.

U.S. Pat. No. 3,311,667 relates to a process for removing benzene from a mixture which is subsequently fed into an isomerization of MCP to cyclohexane. The hydrogenation involves hydrogenating benzene in the presence of a suitable catalyst, for example a metal catalyst on kieselguhr, with hydrogen to cyclohexane. The isomerization of MCP to cyclohexane is performed in the presence of metal halides such as acid-enhanced aluminum halide. This document, however, does not contain any statements as to whether DMP is present and hence the point at which DMP is separated from cyclohexane, or that this removal is problematic.

EP-A 1 995 297 discloses a process and a corresponding apparatus for hydrogenation and decyclization of benzene and the isomerization of $C_5$-$C_6$ paraffins present in a mixture comprising at most 1% by weight of benzene. For hydrogenation of benzene, metallic catalysts can be used, suitable metals being the elements of the platinum group, tin or cobalt and molybdenum. For isomerization of the mixture obtained in the hydrogenation, which may comprise a residual amount of benzene, zeolites in particular are used as the catalyst. In the process described in EP-A 1 995 297, the parameters in the isomerization are adjusted such that opening of the cyclohexane rings obtained in the benzene hydrogenation to isoalkanes is achieved. The primary purpose of this process is thus not the preparation of cyclohexane but the preparation of alkanes having a high degree of branching. In addition, EP-A 1 995 297 also does not contain any statements that an acidic ionic liquid can also be used for isomerization, or that the removal of aromatics, particularly of benzene, prior to the isomerization is advantageous. A similar process to EP-A 1 995 297 is described in EP-A 1 992 673.

U.S. Pat. No. 2,846,485 discloses a process for preparing high-purity cyclohexane and benzene, using a mixture comprising n-hexane, benzene, MCP, cyclohexane and DMP. In a first extractive rectification zone, benzene is separated from the other reactant components. The reactant which has been substantially freed of benzene is combined with a mixture which comprises cyclohexane and MCP and originates from the bottom of a second fractionating rectification zone. The mixture thus combined is fed into a first fractionating rectification zone, with removal of an MCP-containing fraction via the top and a cyclohexane-containing fraction via the bottom.

The overhead product of the first fractionating rectification zone is first conducted into an isomerization zone in which the majority of MCP is isomerized to cyclohexane using Friedel-Crafts catalysts such as aluminum chloride which may additionally comprise HCl. The isomerization product is introduced into the above-described second fractionating rectification zone, in order to remove n-hexane and low boilers as the top product therein. The bottom product from the first fractionating rectification zone is transferred into a second extractive rectification zone in which a cyclohexane-comprising mixture at the bottom is separated from the DMP drawn off via the top.

The process described in U.S. Pat. No. 2,846,485 is disadvantageous, since it is very complex in terms of apparatus (among other aspects). Cyclohexane, the actual process product, from DMP is not removed until the end of the process, since the cyclohexane formed in the isomerization of MCP is recycled into a DMP-containing fraction, meaning that the DMP has to be removed from the entire amount of cyclohexane produced. In this process, moreover, the benzene is first removed in order to obtain it as an independent product. However, the benzene removal is more complex in apparatus terms than the hydrogenation of benzene to cyclohexane by the process of the present invention.

U.S. Pat. No. 3,406,217 relates to a process for preparing cyclohexane from a petroleum/naphtha fraction comprising benzene, methylcyclopentane, cyclohexane and paraffinic hydrocarbons having one to eight carbon atoms. In step a), the (petroleum/)naphtha fraction is introduced into a distillation zone. According to step b), in the distillation zone, i) an intermediate fraction comprising benzene, methylcyclopentane and cyclohexane, ii) an overhead fraction comprising pentanes and comparatively light paraffinic hydrocarbons, and iii) a bottoms fraction comprising heptanes and comparatively heavy paraffinic hydrocarbons are separated from one another. According to step c), the bottoms fraction is passed into a cracking zone where at least a portion of the bottoms fraction is converted to benzene, olefins and diolefins. In step d), a benzene-containing stream is removed from this cracking zone and combined with the intermediate fraction according to step b). From this combined stream according to step d), the paraffin components are removed in step e), in order to produce a "benzene hydrogenation feed stream". The stream is passed through a benzene hydrogenation zone in step f), with conversion of benzene to cyclohexane. The effluent from the benzene hydrogenation zone is passed in step g) through an isomerization zone where methylcyclopentane is converted to cyclohexane. According to step h), cyclohexane is removed from the isomerization zone. In the process according to U.S. Pat. No. 3,406,217, a conventional isomerization catalyst such as an HCl-promoted aluminum halide complex catalyst is used in the isomerization. The separation of the cyclohexane from DMP is of no importance at all in this process, since the starting mixtures used in U.S. Pat. No. 3,406,217 do not comprise any DMP at all.

U.S. Pat. No. 6,503,465 discloses a system for isomerization of a hydrocarbon feedstock comprising saturated $C_6$ hydrocarbons. The system comprises a first isomerization reactor comprising a first isomerization catalyst and a total of 14 different conduit devices in a very complex relationship to one another. In this system, a total of two isomerization reactors and three separators are connected to one another. The sole FIGURE in U.S. Pat. No. 6,503,465 illustrates such a system. In the process, streams which may comprise cyclohexane, isohexane, methylcyclopentane and/or n-hexane are of no importance either. Cyclohexane, however, is not a target product desired; instead, the emphasis is on the recovery of isohexane and/or n-hexane. Hydrogenation of benzene to cyclohexane and the separating problems associated with a cyclohexane/DMP mixture, however, are of no importance in the process according to U.S. Pat. No. 6,503,465.

Ionic liquids are suitable, inter alia, as catalysts for the isomerization of hydrocarbons. A corresponding use of an ionic liquid is disclosed, for example, in WO 2011/069929, where a specific selection of ionic liquids is used in the presence of an olefin for isomerization of saturated hydrocarbons, more particularly for isomerization of methylcyclopentane (MCP) to cyclohexane. A similar process is described in WO 2011/069957, but the isomerization therein is not effected in the presence of an olefin, but with a copper(II) compound.

It is an object of the present invention to provide a novel process for preparing cyclohexane from a hydrocarbon mixture comprising benzene, MCP, DMP and optionally at least one low boiler. In addition, it is to be possible to recover any cyclohexane present in the hydrocarbon mixture and the cyclohexane formed during hydrogenation of benzene.

The object is achieved by a process for preparing cyclohexane, comprising the following steps:
a) hydrogenating a hydrocarbon mixture (HM1), (HM1) comprising i) benzene, ii) methylcyclopentane (MCP), iii) dimethylpentanes (DMP), iv) possibly cyclohexane and v) possibly at least one compound selected from acyclic $C_5$-alkanes, cyclopentane and acyclic $C_6$-alkanes, to obtain a hydrocarbon mixture (HM2) having an elevated amount of cyclohexane compared to (HM1),
b) feeding the hydrocarbon mixture (HM2) into a rectification column (D1),
c) removing a stream (S1) comprising DMP and cyclohexane from the hydrocarbon mixture (HM2) via an outlet of the rectification column (D1), the outlet being below the feed, preferably at the bottom of (D1), to obtain the hydrocarbon mixture (HM2a) having a reduced amount of DMP compared to (HM2),
d) optionally removing at least one compound selected from acyclic $C_5$-alkanes, cyclopentane and acyclic $C_6$-alkanes from the hydrocarbon mixture (HM2a) in a rectification column (D3) to obtain the hydrocarbon mixture (HM2b) having a reduced amount of at least one compound selected from acyclic $C_5$-alkanes, cyclopentane and acyclic $C_6$-alkanes compared to (HM2a).
e) isomerizing the hydrocarbon mixture (HM2a) or optionally the hydrocarbon mixture (HM2b) in the presence of a catalyst to obtain a hydrocarbon mixture (HM3) having an elevated amount of cyclohexane compared to (HM2a) or, if appropriate, compared to (HM2b),
f) isolating cyclohexane from the hydrocarbon mixture (HM3).

The process according to the invention advantageously allows preparation of pure, especially high-purity (on-spec), cyclohexane, the specifications being, for example, those applicable to the use of the cyclohexane for the preparation, known to those skilled in the art, of caprolactam. The process according to the invention is advantageous in terms of apparatus complexity; it is additionally possible to obtain high yields of cyclohexane.

Owing to the (prior) removal of DMP in step c) ("prior DMP removal") before the second part of the cyclohexane preparation process, as a result of isomerization in accordance with step e), the exceptionally complex separation, especially rectification, of DMP out of the cyclohexane process product can at least partly be avoided, especially when the DMP is 2,4-dimethylpentane (2,4-DMP) and it is present in the starting mixture in a concentration of >100 ppm. This distinctly reduces the energy intensity and apparatus complexity in the preparation of pure or high-purity cyclohexane.

The process according to the invention advantageously allows complete or virtually complete removal of the DMP present in the starting mixture by virtue of the (prior) removal from the starting mixture. Particular preference is given to performing the process according to the invention in such a way that the DMP present in the starting mixture is removed completely or virtually completely (down to 2% based on the amount of all DMP isomers present in the starting mixture) from the starting mixture by DMP removal. Alternatively, virtually complete DMP removal from the starting mixture can also be defined by the amount of DMP remaining in the mixture (HM2a) in relation to MCP. Taking this approach, it is especially preferable that the amount of DMP drawn off, preferably via the top, in the rectification apparatus (D1) as mixture (HM2a), based on the sum of the amounts of MCP drawn off via the top, is at most 0.1% by weight, preferably at most 0.02% by weight.

The process according to the invention can be performed irrespective of whether or not cyclohexane is already present in the hydrocarbon mixture (starting mixture) used. If cyclohexane itself is also present alongside DMP in the hydrocarbon mixtures used, this cyclohexane present in the starting mixture and the cyclohexane formed in the benzene hydrogenation in step a), in the process according to the invention, is removed together with DMP, preferably via the bottom. The disadvantage of a reduction in the amount of cyclohexane product, which is associated with this arrangement, however, is more than compensated for by the above-described reduction in energy intensity and apparatus complexity.

In one embodiment of the present invention, however, this cyclohexane present in the hydrocarbon starting mixture can be recovered. In this embodiment, the cyclohexane discharged from the process together with the DMP can be removed again from DMP by distillation, preferably by an extractive or azeotropic rectification. The resulting cyclohexane, which is essentially free of DMP, can be isolated and/or fed back to the process product (cyclohexane which is prepared in step e) by the process according to the invention) or fed into the process according to the invention at another point. The advantage in the case of this process variant over a removal from a point further on in the process (downstream), i.e., for example, from the cyclohexane product stream, is considered to be that the DMP removal has to be conducted from a much smaller amount of cyclohexane, since DMP is removed only from any cyclohexane present in the hydrocarbon starting mixture and the cyclohexane formed in the hydrogenation and not also from the cyclohexane formed in the isomerization, which is a significant part of the actual process product. Accordingly, for this separate DMP/cyclohexane separation, smaller apparatuses and a smaller amount of energy are required.

In addition, in the process according to the invention, owing to the upstream hydrogenation of aromatics, especially of benzene, in step a), the isomerization in step e) can be performed in an advantageous manner. The advantage is considered to be that the aromatics present in (HM1), especially benzene, removed completely or at least substantially by an upstream hydrogenation can be converted to the corresponding saturated hydrocarbons. Accordingly, the deactivation which otherwise occurs in the catalysts used for isomerization, more particularly for isomerization of MCP to cyclohexane, by aromatics, especially by benzene or other unsaturated compounds, which is manifested particularly in the case of the preferred use of acidic ionic liquids as catalysts, is reduced or entirely avoided.

In addition, the hydrogenation of the benzene present in (HM1) has the advantage that the amount of product obtained is increased by the cyclohexane obtained in the hydrogenation of benzene, provided that the cyclohexane that arises in the hydrogenation and is, in accordance with the invention, discharged from the process completely or at least for the most part together with DMP in step c) is recovered again by the above-described DMP/cyclohexane separation.

The removal of the remaining aromatics, especially of benzene, by means of hydrogenation additionally has the additional advantage that the distillative workup steps executed subsequently, especially in optimal step d), are facilitated because the formation of azeotropes of aromatics which otherwise occurs, for example benzene with saturated $C_6$-$C_7$-alkanes, is thus avoided.

In principle, an optional removal of low boilers, i.e. of a majority of the acyclic $C_5$-$C_6$-alkanes and cyclopentane, especially of isohexanes, optionally present in the hydrocarbon mixture (HM1), can be effected at various points in the process. It is particularly advantageous, however, in the case of benzene-containing hydrocarbon mixtures (HM1), to perform the removal of low boilers after the hydrogenation and before the isomerization. This is because a removal of low boilers prior to the hydrogenation would have the disadvantage that the benzene present in the hydrocarbon mixture prior to the hydrogenation forms azeotropes with at least some of the low boilers to be removed and would therefore be removed at least partly together with the low boilers. This would reduce the amount of product by the amount of benzene removed together with the low boilers.

Removal of low boilers after the isomerization would in turn have the disadvantage that the low boilers dilute the hydrocarbons to be isomerized, especially MCP, and would thus lead to a reduction in the space-time yield in the isomerization. In addition, the removal of isohexanes prior to the isomerization is advantageous, since the driving force for the isomerization of n-hexane to isohexanes in the subsequent isomerization stage is thus increased. The isomerization of n-hexane to isohexanes in the isomerization stage is again significant because, owing to the position of the boiling points, n-hexane (standard boiling point 68.7° C.) is much more difficult to remove from MCP (standard boiling point 71.7° C.) than the isohexanes (standard boiling points 49.7 to 63.3° C.). Since, however, the isomerization stage is preferably followed by a distillative separation in which MCP is separated from the cyclohexane formed together with open-chain hexanes and is recycled upstream of or into the isomerization, which again necessitates the discharge of the open-chain hexanes from the process, it is advantageous owing to said position of the boiling points to discharge the open-chain hexanes from the process predominantly in the form of isohexanes, while an accumulation thereof, which is limited by the isomerization of n-hexane, can be accepted.

The process according to the invention also delivers advantages in comparison to processes in which first a prior removal of high boilers and only then a benzene hydrogenation are performed. More particularly, the benzene hydrogenation according to step a) inserted upstream of the DMP/high boiler removal according to step c) in accordance with the invention avoids the formation of azeotropes of aromatics, especially benzene, with saturated $C_6$-$C_7$ alkanes in the subsequent process steps. More particularly, in step c) of the invention, no benzene azeotropes or only very minor benzene azeotropes in quantitative terms are present. All the subsequent steps of the process thus work entirely or at least substantially in aromatics-free mode, which offers advantages from a safety point of view, since aromatic compounds are generally classified as highly toxic (CMR material).

In this connection, with regard to stream (D1) according to step c), it is admittedly the case that the volume of (D1) removed, preferably via the bottom, has been increased by the proportion of benzene which has been hydrogenated to cyclohexane beforehand and is present in the hydrocarbon mixture used. This additionally increases the throughput in the further workup of the stream, which leads to higher energy expenditure and larger apparatuses in the extractive distillation (D2). However, this is compensated for by a reduction in the throughput of the optional low boiler removal and particularly in isomerization.

The stream which is fed to the optional low boiler removal is reduced by the amount of cyclohexane formed from benzene. It generally comprises essentially MCP, comparatively low-boiling components and a little cyclohexane which may be recycled from the product distillation. The smaller amount leads to a reduction in the energy expenditure and smaller apparatus dimensions in the optional step d). This likewise reduces the throughput and hence the apparatus dimensions in the isomerization according to step e). The smaller cyclohexane content in the stream fed to the isomerization has an advantageous effect on the reaction conversion, since an isomerization of MCP to cyclohexane catalyzed by an ionic liquid is an equilibrium reaction. As a result, the dimensions of the apparatuses/reactors in step e) may also be smaller.

The distillative separation of cyclohexane from comparatively low-boiling components according to step f) is likewise less complex as a result of the alteration to the process, which allows an energy saving. Moreover, the distillate stream which is optionally recycled to the low boiler removal becomes smaller.

Overall, it is possible through the alteration to the process (hydrogenation prior to DMP removal) to save on the energy requirement and to reduce the investment costs.

In the context of the present invention, a rectification can be performed in the embodiments known to those skilled in the art (see, for example, Kirk-Othmer Encyclopedia of Chemical Technology, Published Online: 17 Aug. 2001, Vol. 8 p. 739 ff.). The respective rectification techniques are performed in the corresponding apparatuses known to those skilled in the art. The performance of an extractive rectification for separation of close-boiling substances is described, for example, in U.S. Pat. No. 4,053,369, U.S. Pat. No. 4,955,468 or WO 02/22528. Rectification using dividing wall columns is described, for example, in EP1127601 B1.

"Rectification", which is performed in a corresponding rectifying column (rectifying apparatus), also called rectification column or rectification apparatus, is understood to mean the following: in rectification, the vapor produced by rectification is conducted in countercurrent to a portion of the condensate thereof in a rectifying column. In this way, more volatile components are enriched in the top product and less volatile components in the bottom product of the rectifying column.

In the present context, the term "rectification column" also includes secondary apparatuses known in each case to the person skilled in the art, for example one or more reboilers, at least one condenser and optionally vessels and pumps. Accordingly, the withdrawal of streams from the rectification column is understood such that the respective stream is optionally passed through one or more of these secondary apparatuses, optionally also with a change in the state of matter and/or return of a portion of the stream withdrawn. For example, the withdrawal of a stream via the top of the rectification column should be understood such that the vapor stream obtained at the top of the column is at least partly condensed and subsequently divided into a return stream and a top product stream. The top product stream is then equivalent to the stream referred to in simplified form in the text which follows as "stream withdrawn via the top". Analogously, the specification of the feeding of a stream to a rectification column also includes the option that the stream in question, prior to entry into the column itself, passes through one or more secondary apparatuses, for example a preheater or pre-evaporator.

In the context of the present invention, the term "dimethylpentanes" (DMP) is understood to mean all known isomers of dimethylpentane, especially 2,2-dimethylpentane (2,2-DMP: standard boiling point: 79.17° C.), 2,3-dimethylpentane (2,3-DMP; standard boiling point: 89.88° C.), 3,3-dimethylpentane (3,3-DMP; standard boiling point: 86.09° C.) and 2,4-dimethylpentane (2,4-DMP; standard boiling point: 80.52° C.). This means that at least one dimethylpentane isomer is present in the corresponding mixtures or streams in the process according to the invention, preference being given to mixtures of two or more dimethylpentane isomers, one of these isomers preferably being 2,4-dimethylpentane.

In the context of the present invention, the term "compounds having a standard boiling point of 79 to 84° C." is understood to mean all hydrocarbons which, at standard pressure, boil within the range from 79 to 84° C. and which, individually or as a mixture, may at first be present in the hydrocarbon mixture (HM1) in the process according to the invention. In the process according to the invention, one single compound or several of these compounds may be separated from one another. One single compound or several of these compounds may also be referred to separately in the text which follows as a constituent of mixtures or streams. If this is the case, only the specific compounds listed in each case are an obligatory constituent of the corresponding mixture or stream; the other compounds having a standard boiling point of 79 to 84° C. which are not named in the corresponding stream or mixture may (unless stated otherwise or no longer possible, for example owing to a preceding removal) likewise be present in the corresponding stream or mixture. One single compound or several of these compounds may also be covered by the definition of another selection of compounds, for example by the definition of the term "$C_5$-$C_6$-alkanes".

Examples of compounds having a standard boiling point of 79 to 84° C. are cyclohexane (80.78° C.), 2,2-DMP (79.17° C.), 2,4-DMP (80.52° C.), 2,2,3-trimethylbutane (80.87° C.) and benzene (80.08° C.).

The same as stated above for the compounds having a standard boiling point of 79 to 84° C. also applies in the context of the present invention to compounds covered by the term "high boilers having a standard boiling point >84° C.". Examples of high boilers having a standard boiling point >84° C. are 3,3-DMP (86.09° C.), 2,3-DMP (89.88° C.), 2-methylhexane (2-MH; 90.06° C.), 3-methylhexane (3-MH; 91.87° C.) and 3-ethylpentane (3-EP; 9345° C.).

In the context of the present invention, the two aforementioned groups of compounds (compounds having a standard boiling point of 79 to 84° C. and high boilers having a standard boiling point >84° C.) may also be combined to form one group of compounds. In this situation, the compounds are referred to correspondingly as "high boilers having a standard boiling point >78° C.". The above remarks regarding the two individual groups also apply analogously to this group of compounds.

In addition, in the context of the present invention, the group of compounds having a standard boiling point >84° C. may also be included as a subgroup in the group which is referred to as "higher-boiling components than cyclohexane". The latter group thus additionally also includes compounds having a standard boiling point of >80.78° C. up to and including 84° C.

In the context of the present invention, the term "majority" in connection with a stream (feed stream)—unless stated otherwise—means at least 50%, preferably at least 80%, more preferably at least 95%, especially at least 99% by weight.

The process according to the invention for preparation of cyclohexane from methylcyclopentane (MCP) and benzene is defined in detail hereinafter. In this context, reference is also made to FIGS. 1 to 4.

In the context of the present invention, in step a), a hydrocarbon mixture (HM1) is hydrogenated, (HM1) comprising i) benzene, ii) methylcyclopentane (MCP), iii) dimethylpentanes (DMP), iv) possibly cyclohexane and v) possibly at least one compound selected from acyclic $C_5$-alkanes, cyclopentane and acyclic $C_6$-alkanes to obtain a hydrocarbon mixture (HM2) having an elevated amount of cyclohexane compared to (HM1).

The individual components of the hydrocarbon mixture (HM1) may be present in any desired concentrations/ratios relative to one another. The hydrocarbon mixture (HM1) preferably comprises at least 90% by weight, preferably at least 95% by weight, of hydrocarbons having 5 to 8 carbon atoms, provided that the hydrocarbons having 5 to 8 carbon atoms comprise MCP, benzene, DMP possibly cyclohexane and possibly at least one low boiler according to the above components v). It is additionally preferable for the hydrocarbon mixture (HM1) to comprise cyclohexane, preferably to a maximum of 15% by weight. The hydrocarbons may otherwise be saturated or unsaturated and/or cyclic, linear or branched. More particularly, the hydrocarbon mixture (HM1) comprises between 10% by weight and 60% by weight, more preferably between 20% by weight and 50% by weight, of MCP and/or between 1% by weight and 30% by weight, more preferably between 4% by weight and 20% by weight, of benzene.

In a preferred embodiment of the present invention, the hydrocarbon mixture (HM1) comprises benzene, methylcyclopentane (MCP), DMP, cyclohexane and at least one compound selected from acyclic $C_5$-alkanes, cyclopentane and acyclic $C_5$-alkanes. (HM1) may optionally comprise at least one further compound selected from olefins and $C_7$-$C_8$-alkanes. The term "olefin" comprises, as well as linear, monounsaturated olefins such as pentene or hexene, also cyclic olefins, especially cyclohexene, and also dienes and cyclic dienes. The group of the $C_7$-$C_8$-alkanes preferably includes compounds having a standard boiling point >78° C., also called "high boilers" hereinafter. The hydrocarbon mixture (HM1) may optionally also comprise hydrocarbons having more then eight carbon atoms and/or hydrocarbons having a relatively low boiling point, for example those having fewer than five carbon atoms. The same also applies to the presence of further aromatics alongside benzene.

The hydrocarbon mixture (HM1) more preferably comprises benzene, methylcyclopentane (MCP), DMP, cyclohexane, at least one further hydrocarbon selected from n-hexane and isohexanes, and optionally at least one further hydrocarbon selected from n-heptane, isoheptanes, methylcyclohexane and dimethylcyclopentanes.

Owing to step a), benzene is thus hydrogenated to cyclohexane in the process according to the invention. In other words, this means that, in step a), the aromatics present in the hydrocarbon mixture (HM1), i.e. benzene and any other aromatics present, are hydrogenated to obtain the corresponding nonaromatic hydrocarbons, preferably the fully saturated hydrocarbons which arise with retention of all carbon-carbon bonds. If other unsaturated compounds are present in the hydrocarbon mixture (HM1), for example olefins such as cyclohexene, these are likewise hydrogenated in step a) of the present invention.

The hydrogenation of the hydrocarbon mixture (HM1) in step a) is effected, in the context of the present invention, in an apparatus (V) suitable for this purpose, this apparatus preferably comprising at least one hydrogenation reactor (HR). In the apparatus (V), benzene is hydrogenated to cyclohexane, the hydrogenation preferably being effected using elemental hydrogen. It is additionally preferred that the hydrogenation is effected in the liquid phase.

The hydrogenation of benzene to cyclohexane in step a) is generally performed in the presence of a suitable catalyst. Suitable catalysts are in principle all catalysts known to those skilled in the art for this purpose, for example a metal catalyst on kieselguhr according to U.S. Pat. No. 3,311,667 or metallic catalysts according to EP A 1 995 297, wherein the metals used with preference are the elements of the platinum group, tin or cobalt and molybdenum.

Preference is given to performing the hydrogenation in the presence of a catalyst comprising, as an active metal (also referred to as metal component or active component), at least one element of groups 8 to 10 of the Periodic Table of the Elements (PTE), for example iron, cobalt, nickel or ruthenium (corresponds to transition group VIIIB of the CAS Version of the PTE), especially nickel or ruthenium. It is additionally preferable that the active metal is applied to a support material (support). Suitable supports are in principle all supports known to those skilled in the art, for example $SiO_2$-containing, zirconia-containing or alumina-containing supports. Particular preference is given to using a catalyst comprising nickel as an active metal on an alumina-containing support.

The hydrogenation as such is executed and operated in a manner known per se to those skilled in the art, preference being given to a combination of a main reactor operated in an optionally cooled circuit (recycling of a portion of the mixture flowing out of the reactor into the mixture flowing into the reactor, with optional positioning of the cooling unit upstream or downstream of said feed) and a downstream postreactor operated in straight pass, i.e. without recycling. In this case, the apparatus (V) thus comprises two hydrogenation reactors (HR).

The hydrogenation reactors (HR) are preferably designed as fixed bed reactors without internal cooling. In this case, the hydrogenation is preferably operated such that the temperature differential between entering and exiting mixture is monitored continuously and, when this value falls below a particular target value, the entrance temperature is raised. It is additionally preferable that the hydrogenation reactors are operated in trickle mode.

It is additionally preferable that the hydrogenation is followed downstream by an apparatus in which decompression is effected to a pressure below the pressure established in the postreactor. This affords a gas stream which comprises hydrogen dissolved beforehand in the hydrocarbon mixture and is in any case compressed and recycled into at least one of the hydrogenation reactors (HR).

The hydrogenation is preferably performed at a temperature between 50 and 200° C., more preferably between 100 and 180° C., and/or a pressure between 10 and 300 bar abs., more preferably between 30 and 200 bar abs.

It is additionally preferable in the process according to the invention that the overall conversion in the hydrogenation of the benzene (and of any other unsaturated compounds present in the hydrocarbon mixture (HM1)) is at least 90%, more preferably 99%, and/or the residual content of the benzene (and of any other unsaturated compounds present in the hydrocarbon mixture (HM1)) in the hydrocarbon mixture (HM2) is 1% by weight, preferably at most 0.1% by weight, more preferably at most 0.01% by weight.

Owing to the hydrogenation, in step a) of the invention, the hydrocarbon mixture (HM2) is obtained, the composition of which differs from the hydrocarbon mixture (HM1) primarily with respect to the hydrogenated compounds. The hydrocarbon mixture (HM2) thus comprises DMP, cyclohexane, MCP and at least one compound selected from acyclic $C_5$-alkanes, cyclopentane and acyclic $C_6$-alkanes (low boilers). In the hydrocarbon mixture (HM2), components ii), iii) and v) are thus also present, these having already been present in (HM1). In addition, the hydrocarbon mixture (HM2) comprises all other components as per hydrocarbon mixture (HM1) which are not chemically altered in the hydrogenation, and any hydrocarbons formed by hydrogenation of olefins, dienes and of other aromatics.

The hydrocarbon mixture (HM2) preferably comprises cyclohexane, MCP, DMP, not more than 0.1% by weight of aromatics and at least one compound selected from acyclic $C_5$-alkanes, cyclopentane and acyclic $C_6$-alkanes. The hydrocarbon mixture (HM2) more preferably comprises cyclohexane, methylcyclopentane (MCP), DMP, not more than 0.1% by weight of aromatics and at least one further hydrocarbon selected from n-hexane and isohexanes.

In step b) of the process according to the invention, the hydrocarbon mixture (HM2) obtained (in the hydrogenation according to step a)) is fed into the rectification column (D1), which is specified further hereinafter in connection with step c).

In step c) of the process according to the invention, a stream (S1) comprising DMP and cyclohexane is removed from the hydrocarbon mixture (HM2) via an outlet of the rectification column (D1), the outlet being below the feed, preferably at the bottom of (D1), to obtain the hydrocarbon mixture (HM2a) having a reduced amount of DMP compared to (HM2), The hydrocarbon mixture (HM2a) in turn is drawn off via an outlet of the rectification column (D1) above the feed, preferably via the top of (D1).

Preferably, in the rectification column (D1), the DMP and cyclohexane and any other alkanes having 7 or more carbon atoms (high boilers) present in the hydrocarbon mixture (HM2) are removed completely or virtually completely (down to 2% based on the amount of DMP and cyclohexane or high boilers present in (HM2)) from (HM2), more particularly from MCP and any low boilers according to component v) (i.e. the main components of the mixture (HM2a)). The DMP and cyclohexane and any other alkanes having 7 or more carbon atoms are drawn off from the rectification column (D1) as stream (S1), which is preferably present in the bottom of (D1). The cyclohexane likewise present in stream (S1) comprises the cyclohexane which has been formed from benzene in the prior hydrogenation step a) and the cyclohexane which may already have been present in the hydrocarbon mixture (HM1). In contrast, the hydrocarbon mixture (HM2a) preferably does not include any cyclohexane or includes only a relatively small proportion (a maximum of 2% by weight based on (HM2)).

Alternatively, virtually complete high boiler removal, preferably virtually complete DMP removal, from the hydrocarbon mixture (HM2) can also be defined by the amount of high boilers, preferably of DMP, remaining in the mixture (HM2a) in relation to MCP. Taking this approach, it is especially preferable that the amount of high boilers, preferably of DMP, present in the mixture (HM2a), based on the sum of the amounts of MCP present in (HM2a), is at most 0.1% by weight, preferably at most 0.02% by weight.

It is additionally preferable that the hydrocarbon mixture (HM2a) comprises at least 95%, preferably at least 98%, of the portion of MCP present in the hydrocarbon mixture (HM2) and/or that the hydrocarbon mixture (HM2a) comprises at most 0.1% by weight, preferably at most 0.02% by weight (based on the total amount of MCP in (HM2a)), of DMP. The hydrocarbon mixture (HM2a) especially preferably comprises at most 0.015% by weight (based on the total amount of MCP in (HM2a)) of 2,4-DMP.

The rectification columns (D1) used—in steps b) and c) of the invention—may in principle be any rectification columns known to those skilled in the art. It is additionally preferable that the outlet of the rectification column (D1) from which the mixture (HM2a) is removed is above the feed with which the hydrocarbon mixture (HM2) is fed into (D1), the outlet preferably being in the top of (D1).

The stream (S1) removed from the bottom of the rectification column (D1) preferably comprises DMP, cyclohexane and possibly further components. The further components are preferably high boilers having a standard boiling point >78° C.

In the optional step d) of the process according to the invention, at least one compound selected from acyclic $C_5$-alkanes, cyclopentane and acyclic $C_6$-alkanes is removed from the hydrocarbon mixture (HM2a) in a rectification column (D3) to obtain the hydrocarbon mixture (HM2b) having a reduced amount of at least one compound selected from acyclic $C_5$-alkanes, cyclopentane and acyclic $C_6$-alkanes compared to (HM2a). The optional step d) is preferably performed in the process according to the invention when component v) is present in the hydrocarbon mixture (HM1) used in the hydrogenation according to step a).

This removal in step d) is also referred to hereinafter as "low boiler removal". "Low boilers" are understood to mean especially cyclopentane and acyclic $C_5$-$C_6$-alkanes such as isohexanes.

The hydrocarbon mixture (HM2b) depleted of the low boilers is subsequently sent to the isomerization in step e) of the present invention. If no low boilers are removed in optional step d), instead of (HM2b), the hydrocarbon mixture (HM2a) is sent to the isomerization according to step e). The hydrocarbon mixture (HM2b) depleted of the low boilers is removed via a takeoff point below the feed, preferably from the bottom of the corresponding rectification column.

Preference is given to performing the low boiler removal in such a way that a stream (LB1) comprising at least one compound selected from linear or branched $C_5$-alkanes, cyclopentane and linear or branched $C_6$-alkanes, more preferably isohexanes, is separated by distillation from the hydrocarbon mixture (HM2a). The stream (LB1) is preferably drawn off via a takeoff point above the feed, more preferably via the top of the rectification column.

In the rectification column (D3), the low boilers are removed from the hydrocarbon mixture (HM2a) as stream (LB1), stream (LB1) boiling at a lower temperature than (HM2a). Stream (LB1), compared to (HM2a), is preferably enriched in isohexanes and/or cyclopentane and depleted of MCP and any cyclohexane present. The hydrocarbon mixture (HM2b) depleted of/reduced by stream (LB1) boils at a higher temperature than (HM2a). The hydrocarbon mixture (HM2b), compared to (HM2a), is preferably depleted of isohexanes and/or cyclopentane and enriched in MCP and any cyclohexane present.

The low boiler removal is preferably executed and operated in such a way that stream (LB1) comprises less than 5% by weight, more preferably less than 2.5% by weight, of MCP and the hydrocarbon mixture (HM2b) comprises less than 10% by weight, more preferably less than 5% by weight, of isohexanes.

Stream (LB1) can, for example, be introduced into a steamcracker as what is called cracker cofeed. Optionally, within the low boiler removal, it is possible to draw off a further stream depleted of isohexanes and enriched in components having a lower boiling point than the isohexanes, for example chlorinated paraffins having <4 carbon atoms per molecule, compared to stream (LB1).

Preference is also given to an embodiment in which preferably a stream (LB2) originating from step f) according to the description which follows is recycled fully or partly into or upstream of (D3).

In step e) of the process according to the invention, the hydrocarbon mixture (HM2a) is isomerized in the presence of a catalyst, preferably of an acidic ionic liquid, to obtain a hydrocarbon mixture (HM3) having an elevated amount of cyclohexane compared to (HM2a). Owing to step e), MCP is thus isomerized to cyclohexane in the process according to the invention. If the optional step d) is performed in accordance with the invention, the isomerization is effected correspondingly with the hydrocarbon mixture (HM2b) rather than with (HM2a).

The isomerization of MCP to cyclohexane in step e) is effected in the presence of a catalyst. Suitable catalysts are in principle all catalysts known for this purpose to those skilled in the art, for example Friedel-Crafts catalysts according to U.S. Pat. No. 2,846,485 such as aluminum chloride which may additionally contain HCl, or metal halides according to U.S. Pat. No. 3,311,667 such as aluminum chloride, zirconium chloride or boron trifluoride. Additionally suitable as catalysts are also the zeolites used in EP-A 1 995 297, or ionic liquids as used, for example, in WO 2011/069929.

In the context of the present invention, the isomerization is preferably effected in the presence of an acidic ionic liquid having the composition $K1Al_nX_{(3n+1)}$ where K1 is a monovalent cation, X is halogen and 1<n<2.5. For example, mixtures of two or more acidic ionic liquids may be used, preference being given to using one acidic ionic liquid.

K1 is preferably an unsubstituted or at least partly alkylated ammonium ion or a heterocyclic (monovalent) cation, especially a pyridinium ion, an imidazolium ion, a pyridazinium ion, a pyrazolium ion, an imidazolinium ion, a thiazolium ion, a triazolium ion, a pyrrolidinium ion, an imidazolidinium ion or a phosphonium ion. X is preferably chlorine or bromine.

The acidic ionic liquid more preferably comprises, as a cation, an at least partly alkylated ammonium ion or a heterocyclic cation and/or, as an anion, a chloroaluminate ion having the composition $Al_nCl_{(3n+1)}$ where $1<n<2.5$. The at least partly alkylated ammonium ion preferably comprises one, two or three alkyl radicals (each) having one to ten carbon atoms. If two or three alkyl substituents are present with the corresponding ammonium ions, the respective chain length can be selected independently; preferably, all alkyl substituents have the same chain length. Particular preference is given to trialkylated ammonium ions having a chain length of one to three carbon atoms. The heterocyclic cation is preferably an imidazolium ion or a pyridinium ion.

The acidic ionic liquid especially preferably comprises, as a cation, an at least partly alkylated ammonium ion and, as an anion, a chloroaluminate ion having the composition $Al_nCl_{(3n+1)}$ where $1<n<2.5$. Examples of such particularly preferred acidic ionic liquids are trimethylammonium chloroaluminate and triethylammonium chloroaluminate.

Furthermore, in the isomerization, in addition to the acidic ionic liquid, it is also possible to use a hydrogen halide (HX) as a cocatalyst. The hydrogen halides (HX) used may in principle be any conceivable hydrogen halides, for example hydrogen fluoride (HF), hydrogen chloride (HCl), hydrogen bromide (HBr) or hydrogen iodide (HI). The hydrogen halides can optionally also be used as a mixture, but preference is given in the context of the present invention to using only one hydrogen halide. Preference is given to using the hydrogen halide whose halide moiety is also present in the above-described acidic ionic liquid (at least partly) in the corresponding anion. The hydrogen halide (HX) is preferably hydrogen chloride (HCl) or hydrogen bromide (HBr). The hydrogen halide (HX) is more preferably hydrogen chloride (HCl).

The apparatus (IV) used for performance of the isomerization may in principle be any apparatuses known to the person skilled in the art for such a purpose. The apparatus (IV) is preferably a stirred tank or a stirred tank cascade. A "stirred tank cascade" means that two or more, for example three or four, stirred tanks are connected in succession (in series).

The isomerization is preferably performed at a temperature between 0° C. and 100° C., especially preferably at a temperature between 30° C. and 60° C. It is additionally preferred that the pressure in the isomerization is between 1 and 20 bar abs. (absolute), preferably between 2 and 10 bar abs.

The performance of the isomerization of MCP in step e) in the presence of an acidic ionic liquid as a catalyst and optionally a hydrogen halide as a cocatalyst is known to those skilled in the art. The hydrocarbons (i.e. MCP, cyclohexane and any other hydrocarbons present in (HM2a)) and the ionic liquid in the isomerization preferably each form a separate phase, though portions of the ionic liquid may be present in the hydrocarbon phase and portions of the hydrocarbons in the ionic liquid phase. If present, the hydrogen halide, especially hydrogen chloride, is introduced, preferably in gaseous form, into the apparatus (IV) for performance of the isomerization. The hydrogen halide may, at least in portions, be present in the two aforementioned liquid phases and in a gaseous phase which is preferably additionally present.

Preference is given to performing the isomerization in the apparatus (IV) in such a way that two liquid phases and one gas phase are present in a stirred tank or a stirred tank cascade. The first liquid phase comprises the acidic ionic liquid to an extent of at least 90% by weight and the second liquid phase comprises the hydrocarbons to an extent of at least 90% by weight. The gas phase comprises at least one hydrogen halide, preferably hydrogen chloride, to an extent of at least 90% by weight. Optionally, a solid phase may also be present, this comprising components from which the ionic liquid is formed in solid form, for example $AlCl_3$. The pressure and composition of the gas phase are set here such that the partial pressure of the gaseous hydrogen halide, especially of HCl gas, in the gas phase is between 0.5 and 20 bar abs. (absolute), preferably between 1 and 10 bar abs.

It is additionally preferable in the context of the present invention that the isomerization is performed in a dispersion (D1), with dispersion of phase (B) in phase (A) in dispersion (D1), the volume ratio of phase (A) to phase (B) being in the range from 2.5 to 4:1 [vol/vol], phase (A) comprising >50% by weight of at least one acidic ionic liquid, and phase (B) comprising >50% by weight of at least one nonaromatic hydrocarbon. It is additionally preferable that the dispersion (D1) additionally comprises HCl and/or gaseous HCl is introduced into the dispersion (D1).

As already stated above, in the isomerization in the presence of an acidic ionic liquid and optionally of a hydrogen halide (HX). MCP is isomerized to cyclohexane or (at least partly) chemically converted. Further hydrocarbons present in (HM2a) or optionally in (HM2b) apart from MCP may also be isomerized. The hydrocarbons obtained in the isomerization are present in the hydrocarbon mixture (HM3). Mixture (HM3) thus differs in terms of composition and/or amount of the hydrocarbons present therein from the corresponding hydrocarbon mixture (HM2a) or optionally (HM2b) present prior to the isomerization. The hydrocarbon mixtures (HM2a) and (HM2b) have already been defined above. However, all components of the hydrocarbon mixtures (HM2a) and (HM2b) which are not isomerized in step e) are likewise present in the hydrocarbon mixture (HM3).

Since the isomerization to be performed in such isomerization processes usually does not proceed to an extent of 100% (i.e. to completion), the product generally still also comprises the hydrocarbon with which the isomerization has been performed (in a smaller amount than before the isomerization). Since, in the present case, MCP is isomerized to cyclohexane, the isomerization product generally comprises a mixture of cyclohexane and (in a smaller amount than before the isomerization) MCP.

The hydrocarbon mixture (HM3) preferably comprises cyclohexane, MCP and possibly acyclic $C_5$-$C_6$-alkanes (low boilers) and/or possibly higher-boiling components than cyclohexane. The low boilers and/or high boilers optionally still present in the hydrocarbon mixture (HM3) may be compounds which had been present in the hydrocarbon mixture (HM1) originally used and have not been removed completely in the preceding process steps, more particularly in steps c) and d), from the corresponding hydrocarbon mixtures. In addition, the compounds may also be those which have formed, preferably as by-products, in the hydrogenation in step a) and/or in the isomerization in step e). The higher-boiling components than cyclohexane, optionally present in (HM3) may also be constituents of any residual amount of aromatics or olefins still present after the hydrogenation in step a). The hydrocarbon mixture (HM3) more preferably comprises cyclohexane, methylcyclopentane (MCP), not more than 0.1% by weight of aromatics and at least one further hydrocarbon selected from n-hexane and isohexanes.

In step f) of the process according to the invention, cyclohexane is isolated from the hydrocarbon mixture (HM3). Step f) is preferably performed in a rectification column (D4) by removing a stream (LB2) comprising MCP and possibly acyclic $C_5$-$C_6$-alkanes from the hydrocarbon mixture (HM3) in (D4) and fully or partly recycling stream (LB2) to step d) or to step e).

The cyclohexane can be isolated by methods known to those skilled in the art, for example using one or more rectification columns into which the output from the apparatus in which the isomerization in step e) has been performed is introduced. In general, in the process according to the invention, in step f)—after the isomerization in step e)—cyclohexane is isolated in a purity of at least 98% by weight, preferably of at least 99.5% by weight, more preferably of at least 99.9% by weight.

Preference is given to performing step f) of the process according to the invention in such a way that the hydrocarbon mixture (HM3) comprising cyclohexane, MCP, possibly acyclic $C_5$-$C_6$-alkanes and possibly higher-boiling components than cyclohexane is fed into a rectification column (D4), and the majority of the MCP and, if present, of acyclic $C_5$-$C_6$-alkanes present in the feed to (D4) is removed from (D4) at a withdrawal point above the feed, preferably via the top. If acyclic $C_5$-$C_6$-alkanes are present in (HM3), these are preferably n-hexane and isohexanes. This stream comprising the majority of MCP (and possibly of acyclic $C_5$-$C_6$-alkanes) is also referred to hereinafter as stream (LB2).

Stream (LB2) is further characterized in that it (relative to (HM3)) is enriched in MCP and depleted of cyclohexane, this stream (LB2) preferably comprising less than 20% by weight, preferably less than 10% by weight, more preferably less than 7% by weight, of cyclohexane.

Stream (LB2) is additionally preferably recycled fully or partly to step d) or to step e), preference being given to fully recycling stream (LB2). The recycling of stream (LB2) to optional step d) or to step e) is generally performed in such a way that stream (LB2) is recycled into or upstream of the corresponding apparatuses for performance of these process steps. Stream (LB2) can thus be recycled into or upstream of the apparatus for performance of the low boiler removal in step d) and/or stream (LB2) can be recycled into or upstream of the apparatus for performance of the isomerization in step e). If stream (LB2) is recycled upstream of the apparatus for performance of the low boiler removal, this means that stream (LB2) is introduced into the hydrocarbon mixture (HM2a) outside the rectification apparatus (D3) in which the optional step d) is performed. If stream (LB2) is recycled upstream of the apparatus for performance of the isomerization, this means that stream (LB2) is introduced into the hydrocarbon mixture (HM2a) or possibly (HM2b), if the optional step d) is performed, outside the apparatus (V) in which the isomerization in step e) is performed.

More particularly, stream (LB2) is recycled to step d), stream (LB2) preferably being introduced into the hydrocarbon mixture (HM2a) upstream of the rectification apparatus (D3) in which step d) is performed.

The cyclohexane can be drawn off from the rectification column (D4), preferably if no higher-boiling components than cyclohexane are present in a concentration which impairs the respective specification, in a purity of at least 98% by weight, preferably of at least 99.5% by weight, more preferably of at least 99.9% by weight, via the bottom of (D4) or a side draw from (D4) below the feed, preferably a vaporous side draw from (D4) (option f0)). If the cyclohexane is drawn off via a preferably vaporous side draw below the feed, a high boiler stream (S5) can be drawn off via the bottom of (D4).

Alternatively, it is also possible to implement option f1), wherein the cyclohexane-enriched stream drawn off via the bottom of (D4) is introduced into a rectification column (D5), and a stream (S5) comprising higher-boiling components than cyclohexane is removed via the bottom of (D5) and cyclohexane is drawn off with a purity of at least 98% by weight, preferably of at least 99.5% by weight, more preferably of at least 99.9% by weight, via a takeoff point above the feed to (D5), preferably via the top.

Alternatively, it is also possible to implement option f2), wherein a cyclohexane-enriched stream, which is preferably in vaporous form, is removed via the side draw from the rectification column (D4), the side draw preferably being in the stripping section of (D4) and/or the cyclohexane-enriched stream from the side draw of (D4) being passed into an apparatus (D6) for further purification, preferably in the form of a rectification column, and cyclohexane being obtained therein via a takeoff point above the feed of (D6), preferably via the top, with a purity of at least 98% by weight, preferably of at least 99.5% by weight, more preferably of at least 99.9% by weight.

In option f2), it is additionally preferable that the feed of the preferably vaporous stream from (D4) to (D6) is below the lowermost tray, the lowermost structured packing element or the lowermost random packing element of (D6), and (D6) is operated with a top condenser and partial reflux of the condensate drawn off therefrom, but not with a dedicated reboiler, and that the liquid obtained at the bottom in (D6) is passed back into the rectification column (D4) at about the level of the side draw. In this embodiment, a stream (S5) comprising higher-boiling components than cyclohexane is drawn off via the bottom of (D4).

Alternatively, it is also possible to implement option f3), wherein the rectification column (D4) takes the form of a dividing wall column, the dividing wall is partly above the feed point, a draw point is in the region of the dividing wall and this draw point is used to withdraw a preferably liquid cyclohexane stream having a purity of at least 98% by weight, preferably of at least 99.5% by weight, more preferably of at least 99.9% by weight. In this embodiment, a stream (S5) comprising higher-boiling components than cyclohexane is likewise drawn off via the bottom of (D4).

Figure 4:
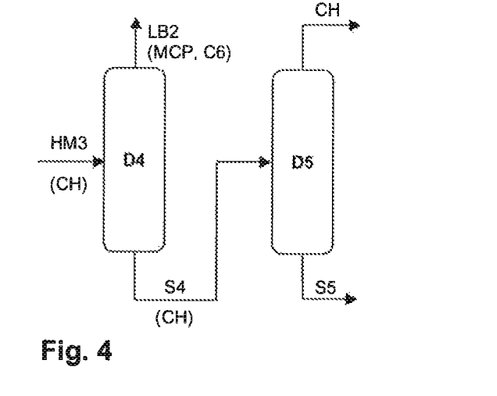
FIG. 4 relates to a specific configuration of the isolation of cyclohexane in step f). All figures are explained in detail at the appropriate point in the text which follows.

FIG. 4 once again illustrates step f) of the process according to the invention as per the above-described option f1). CH means cyclohexane, C6 means acyclic $C_5$-$C_6$-alkanes, especially isohexanes, and the bracketed expressions indicate the components most relevant to the process and/or the main components of the respective stream. In the embodiment according to FIG. 4, a hydrocarbon mixture (HM3) comprising cyclohexane, MCP, acyclic $C_5$-$C_6$-alkanes, especially isohexanes, and high boilers having a standard boiling point >84° C. is used. From the bottom of D4, a cyclohexane-enriched stream (S4) is introduced into the rectification column (D5), from which on-spec cyclohexane is isolated via the top. The bottom stream (S5) comprises higher-boiling components than cyclohexane.

In the context of the present invention, after the isomerization in step e) and prior to a distillative removal/isolation of the cyclohexane in step f), additional purification steps may be performed with the output from the isomerization.

These purification steps may, for example, be a neutral and/or alkaline wash, which can be performed in one or more stages. Additionally or alternatively to the wash, it is also possible to use specific apparatuses, for example distillation or rectification apparatuses, in order, for example, to separate hydrogen halide present from the hydrocarbons. Such apparatuses also comprise apparatuses for one-stage evaporation, especially for flash evaporation. Additionally or alternatively, in the case of use of acidic ionic liquid, it is also possible to connect phase separation units, preferably phase separators, upstream of the aforementioned specific apparatuses, especially in order to separate the acidic ionic liquid from the hydrocarbons.

In a particularly preferred embodiment, the output from the isomerization is conducted into a phase separation unit, for example a phase separator, where a separation into a phase consisting to an extent of at least 90% by weight of acidic ionic liquid and a phase consisting to an extent of at least 90% by weight of hydrocarbons is performed. The phase consisting to an extent of at least 90% by weight of acidic ionic liquid is at least partly recycled into the isomerization and the phase consisting to an extent of at least 90% by weight of hydrocarbons is, after volatile constituents, for example HCl, have optionally been withdrawn therefrom in a distillation or rectification apparatus, conducted into a neutral and/or alkaline wash, where residues of the ionic liquid or constituents thereof, for example HCl or $AlCl_3$, are removed.

Figure 1:
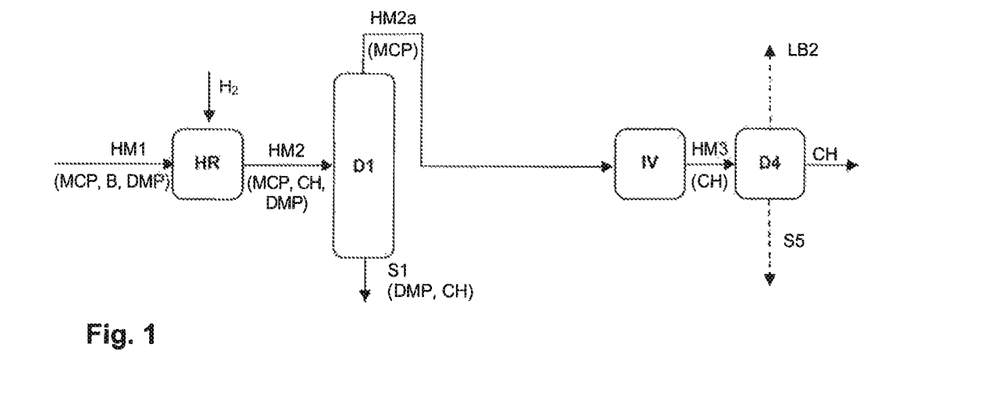
FIG. 1 shows the process according to the invention in its basic form, wherein, in the isolation of cyclohexane according to step f), any low boilers and/or high boilers present are separated from cyclohexane in an apparatus (D4). The removal of cyclohexane from (D4) is shown merely schematically in FIG. 1 (for example, this is effected according to FIG. 4).

FIG. 1 illustrates the process according to the invention once again in its basic form, including steps a) to f), but no low boiler removal is performed according to optional step d). An equivalent process including the optional step d) is shown as a preferred embodiment in FIG. 2. CH means cyclohexane, B means benzene, HR means hydrogenation reactor and IV means isomerization apparatus. The isomerization is preferably performed in a stirred tank or a stirred tank cascade. The hydrocarbon mixture (HM1) comprises benzene, MCP, DMP and at least one low boiler. If (HM1) additionally comprises cyclohexane, this is drawn off from the process together with DMP via stream (S1). In this case, the cyclohexane and/or the cyclohexane that arises in the hydrogenation in step a) can be recovered again, as illustrated hereinafter by the preferred embodiment in conjunction with FIG. 3. In an analogous manner—as detailed above for FIG. 4—only the most important constituents in each case in the corresponding streams or mixtures are listed in brackets in FIGS. 1 to 3 as well.

Figure 2:
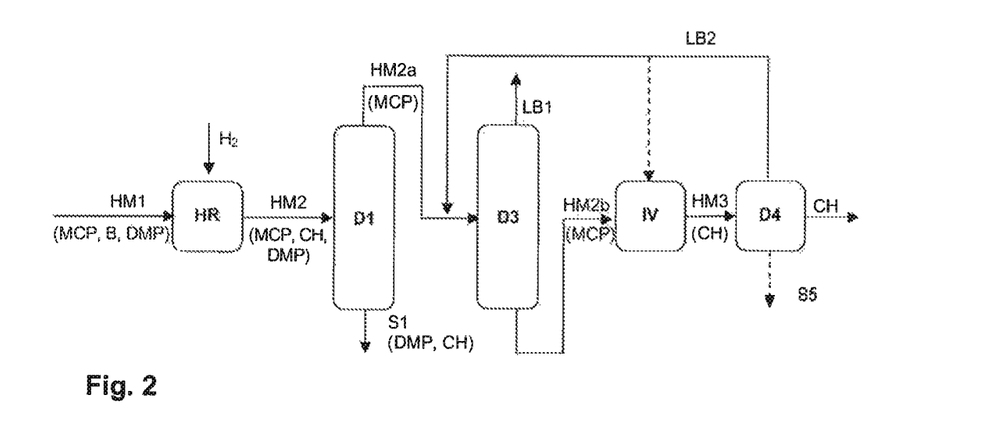
FIG. 2 shows a preferred embodiment of the process of the invention with intermediate low boiler removal according to step d), showing two variants of the return of unisomerized MCP in step f).

Subsequently, cyclohexane is isolated in step f) from the isomerization product according to step e), for example using one or more rectification columns, into which the output of the isomerization apparatus (IV) is introduced; cyclohexane is separated therein from unconverted MCP and any further components, and preferably—as shown in FIG. 2—the MCP-enriched and cyclohexane-depleted substream (LB2) is recycled to step d) and/or to step e). Preference is given to returning (LB2)—as shown in FIG. 2—to step d), especially by introduction into the hydrocarbon mixture (HM2a) upstream of the rectification apparatus (D3). The option of returning (LB2) to step e) is indicated in FIG. 2 by the dotted line (return to the isomerization apparatus (IV)). Step f) is shown in FIG. 1 in simplified form by the rectification apparatus (D4). Preference is given to performing step f) as described above in connection with FIG. 4. Accordingly, FIG. 1 indicates the optional removal of higher-boiling components than cyclohexane via stream (S5) as a possible variant by means of the dotted arrow.

The hydrocarbon mixture (HM1) used in the process according to the invention in step a) may originate from any desired sources. For instance, it is conceivable that (HM1), prior to performance of the process according to the invention, is mixed together from the individual components or that a hydrocarbon mixture (HM1) is produced by combining a plurality of individual mixtures. Preferably, in the context of the present invention, the hydrocarbon mixture (HM1) originates fully or partly from a steamcracking process.

It is additionally preferable that (HM1) is obtained in an apparatus for aromatics removal connected downstream of a steamcracking process, from a stream (S6) originating from the steamcracking process. This means that, in the context of the present invention, the hydrocarbon mixture (HM1) is preferably obtained from an apparatus for aromatics removal.

Apparatuses for aromatics removal as such are known to those skilled in the art; they may comprise, for example, one, two or more interconnected rectification apparatuses. The aromatics removal is preferably performed as an extractive aromatics rectification, especially as an extractive benzene rectification. As already mentioned above, however, a portion of the hydrocarbon mixture (HM1) and/or individual components present therein may originate from a source other than the apparatus for aromatics removal. For example, these portions and/or individual components can subsequently be added to the hydrocarbon mixture (HM1) obtained in the apparatus for aromatics removal.

The apparatus for aromatics removal in turn is preferably connected downstream of a steamcracking process. A stream (S6) originating from the steamcracking process is introduced into the apparatus for aromatics removal. In the apparatus for aromatics removal, stream (S6) is separated into an aromatics-rich stream (S7) and the hydrocarbon mixture (HM1).

The performance of a steamcracking process as such is known to those skilled in the art. In the context of the present invention, the steamcracking process preferably comprises a naphtha cracker (naphtha steamcracking process). Stream (S6) thus preferably originates from a naphtha cracker and/or stream (S6) comprises pyrolysis gasoline or a substream separated from the pyrolysis gasoline.

Stream (S6) is also referred to as the feed stream (S6) to the apparatus for aromatics removal. Stream (S6) comprises the hydrocarbon mixture (HM1) and additionally a proportion of aromatics. These additional aromatics are thus separated from the hydrocarbon mixture (HM1) in the apparatus for aromatics removal. This additionally means that the hydrocarbon mixture (HM1) has a lower concentration of aromatics than the feed stream (S6) to the apparatus for aromatics removal; for example, hydrocarbon mixture (HM1) may have a concentration of aromatics at least 50% lower than the feed stream (S6) to the apparatus for aromatics removal.

Especially when stream (S6) comprises pyrolysis gasoline or a substream separated from the pyrolysis gasoline, the aromatics separation in the context of the present invention may also be preceded by a separation into fractions enriched in benzene, in toluene and in xylenes, optionally supplemented by further process steps. In this case, the benzene-enriched fraction is to be understood as stream (S6).

The benzene-enriched fraction is then preferably separated by means of extractive rectification, for example using N-formylmorpholine as an assistant, into a stream comprising benzene in high purity and a benzene-depleted stream, which is also referred to as C6 nonaromatic stream (C6-NA).

In this case, the hydrocarbon mixture (HM1) according to the present invention can be equated with the C6 nonaromatic stream (C6-NA).

C6-NA may comprise:
- linear open-chain and/or branched and cyclic (naphthenic) C5 hydrocarbons, for example n-pentane, isopentanes, cyclopentane,
- linear open-chain and/or branched and cyclic (naphthenic) C6 hydrocarbons, for example n-hexane, isohexanes, methylcyclopentane (MCP),
- linear open-chain and/or branched and cyclic (naphthenic) C7 hydrocarbons, for example n-heptane, isoheptanes, for example dimethylpentanes (DMP), methylcyclohexane (MCP),
- olefins and/or aromatics, the structure of which is derived from one or more of the aforementioned hydrocarbons by means of elimination of hydrogen, for example benzene or cyclohexene.

In a preferred embodiment of the process according to the invention, the stream (S1) obtained in step c) is introduced into a rectification apparatus (D2), with separation of cyclohexane from DMP in (D2). The embodiment can also be performed when (no) cyclohexane is present in the hydrocarbon mixture (HM1) used in step a), and the cyclohexane is only obtained by the hydrogenation of benzene in step a).

In this embodiment of the process according to the invention, the cyclohexane present in stream (S1) is separated from DMP and from any other components present in stream (S1), for example from the high boilers. The specific composition of stream (S1) has already been described above in connection with step c) of the invention.

The rectification or the rectification apparatus (D2) may have one or more stages, for example two or three stages; it preferably has three stages. In this context, the number of stages is understood to mean the number of columns, in each case including secondary apparatuses, for example reboilers and condensers, which together form the rectification apparatus (D2). A three-stage rectification apparatus (D2) thus means that a total of three columns, in each case including secondary apparatuses, for example reboilers and condensers, in each of which a rectification process can be performed, together form the rectification apparatus (D2). Preferably, (D2) comprises one extractive rectification column. It is additionally preferable that the cyclohexane-enriched stream drawn off from (D2) comprises at most 0.1% by weight, preferably at most 0.02% by weight, of DMP, more preferably at most 0.015% by weight of 2,4-DMP.

If the rectification apparatus (D2) comprises an extractive rectification column, the extractive rectification is preferably effected using an extraction aid (extraction assistant). The extraction aids used are generally compounds for which the following formula (1) applies:

$$\gamma_{DMP,E}^{\infty}/\gamma_{CH,E}^{\infty} > n \qquad (1)$$

where
$\gamma_{DMP,E}^{\infty}$ = activity coefficient of 2,4-dimethylpentane in the extraction aid at infinite dilution,
$\gamma_{CH,E}^{\infty}$ = activity coefficient of cyclohexane in the extraction aid at infinite dilution,
n = preferably 1.1, more preferably 1.3.

The extraction aids used are preferably oxygen-containing open-chain or cyclic organic compounds having a boiling point at least 5 K above that of cyclohexane (81° C.), especially those comprising an amide function R—CO—NR'R" as a structural element, where R, R' and R" are (each independently) preferably selected from $C_1$-$C_{30}$-alkyl and H. Particularly suitable extraction aids are N-methylpyrrolidone and N-formylmorpholine. However, other compounds are also suitable, such as sulfolane, dimethyl sulfoxide and other compounds known to those skilled in the art as aprotic polar solvents. Also suitable are mixtures of a plurality of the compounds mentioned with one another or with water.

The cyclohexane/DMP separation preferably comprises the following steps i) to iii), the rectification apparatus (D2) being formed by the three components (D2-1) to (D2-3):
i) a rectification column (D2-1) in which the majority of the high boilers having a standard boiling point >84° C. (based on the amount in the feed to (D2-1)) is removed via the bottom and the majority of the cyclohexane and other compounds having a standard boiling point of 79 to 84° C. (based on the amount in the feed to D2-1) via the top,
ii) an extractive rectification column (D2-2) in which the top product from (D2-1) is combined with an extraction aid and distilled in such a way that the majority of the extraction aid and of the cyclohexane are drawn off via the bottom and the majority of the other compounds having a standard boiling point of 79 to 84° C. present in the top product from (D2-1) are drawn off from (D2-2) via the top, and
iii) a regeneration column (D2-3) in which the majority of the cyclohexane present in the bottom stream from (D2-2) is drawn off via the top and the majority of the extraction aid present in the bottom stream from (D2-2) via the bottom.

In the context of the above steps i) to iv), the phrase "via the bottom" means a takeoff point below the feed, preferably the bottom, and the phrase "via the top" a takeoff point above the feed, preferably the top of the respective column.

Optionally, in this embodiment, an optional step iv) may be performed in connection with steps i) to iii), said step iv) being defined as follows:
iv) optionally a hydrogenation apparatus into which either stream (S1) or the top product from (D2-3) is conducted.

However, this embodiment is preferably performed without the optional hydrogenation step iv).

The optional step iv) included in the above embodiment is generally performed only when stream (S1) comprises unsaturated compounds which are thus also fed into the rectification apparatus (D2) and which are additionally not discharged from the process via the bottom of the rectifying column (D2-1). The hydrogenation in the optional step iv) can be performed analogously to the hydrogenation in the above-described step a), preferably in one stage. The hydrogenation apparatus may optionally also be connected upstream of the rectification apparatus (D2). In this case, stream (S1) is first conducted into the rectification apparatus, then the hydrogenated stream (S1) is introduced into the rectification apparatus (D2), especially into the rectifying column (D2-1). This is an advantageous variant when stream (S1) comprises components, for example unsaturated hydrocarbons, which form azeotropes with the components to be drawn via the bottom of (D2-1).

The above-described preferred embodiment of the cyclohexane/DMP separation can optionally also be performed without a rectifying column (D2-1) as an obligatory constituent. In this variant, the cyclohexane/DMP separation is effected analogously using only the two columns (D2-2) and (D2-3), in which case there may optionally also be a downstream hydrogenation apparatus. This variant is preferably performed when stream (S1) comprises only a small proportion of, if any, high boilers having a standard boiling point >84° C.

The above-described preferred embodiment using the extractive rectification column (D2-2) is preferably executed and operated in such a way that the DMP-containing stream drawn off via the top of (D2-2) comprises less than 50% by weight, preferably less than 10% by weight, of cyclohexane. In addition, the cyclohexane-containing stream drawn off via the top of regeneration column (D2-3) comprises preferably less than 1% by weight, more preferably less than 10 ppm by weight, of extraction aid and/or less than 1% by weight, preferably less than 300 ppm by weight, of dimethylpentanes, more preferably less than 150 ppm by weight of 2,4-dimethylpentane.

It is additionally preferable that cyclohexane is isolated in a purity of 98% by weight, especially at least 99.5% by weight, from (D2). With regard to the performance of the isolation of the cyclohexane, the same considerations apply as detailed above in connection with the isolation of the cyclohexane in step f), especially in connection with the rectification apparatus (D4). Alternatively, the cyclohexane which originates from the rectification apparatus (D2) in the present preferred embodiment can be combined with the cyclohexane which has been prepared in the isomerization in step e).

Figure 3:
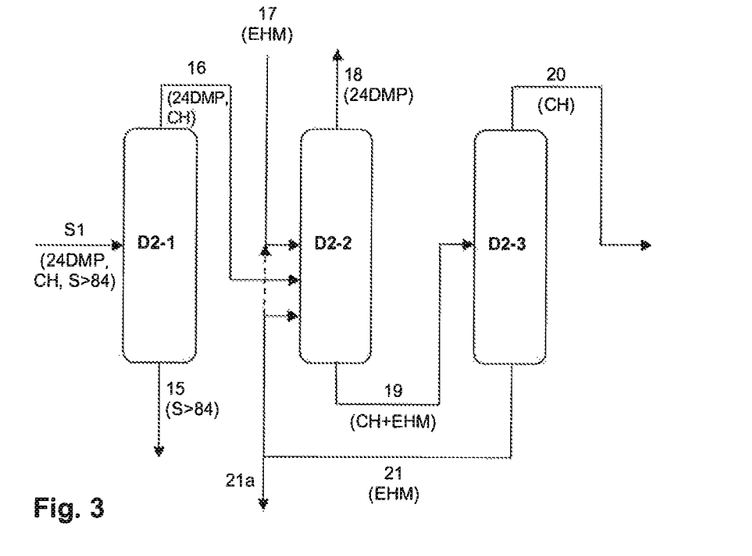
FIG. 3 shows a specific configuration for recovery of cyclohexane which is formed in the hydrogenation of benzene and is optionally additionally already present together with DMP in the hydrocarbon mixture (HM1).

The above-described preferred embodiment of the present invention is additionally illustrated in a preferred embodiment in conjunction with FIG. 3. In FIG. 3, the abbreviations, arrows and other symbols have analogous meanings to those explained above for FIG. 1 or in the description of this preferred embodiment. In the embodiment according to FIG. 3, a rectification apparatus (D2) consisting essentially of three columns ((D2-1) to D2-3)) is used. This embodiment may optionally also additionally be connected downstream of a hydrogenation apparatus (not shown in FIG. 3). The individual columns may additionally also have secondary apparatuses, such as reboilers or condensers, which are not shown in FIG. 3 for the sake of clarity. EHM means extraction aid, S>84 means high boilers having a standard boiling point >84° C., 24DMP means 2,4-dimethylpentane and the bracketed expressions indicate the components most relevant to the process and/or the main components of the respective stream. 24DMP is mentioned by way of example as a preferred component of the (other) compounds having a standard boiling point of 79 to 84° C. The extraction aid used is preferably N-methyl-2-pyrrolidone (NMP).

Stream (S1) which originates with preference from the bottom of the rectification apparatus (D1) and comprises DMP, cyclohexane and possibly high boilers having a normal boiling point >78° C., is had into the rectifying column (D2-1). In (D2-1), the cyclohexane present in stream (S1) is concentrated, by first separating stream (S3) by means of rectification into a stream 15 enriched in higher-boiling components than cyclohexane (i.e., for example, 3,3-DMP and other high boilers having a standard boiling point >84° C. and a stream 16 depleted of higher-boiling components than cyclohexane (stream 16 thus comprises cyclohexane and a majority of the other compounds having a boiling point of 79 to 84° C. and a residual amount of high boilers having a standard boiling point >84° C.). Stream 15 can, for example, be conducted as a cofeed to a steamcracking process or be used as a constituent of fuel mixtures.

Stream 16 is conducted into an extractive rectification column (D2-2). At a point above the feed of stream 16, a stream 17 comprising at least one extraction aid (EHM) is conducted into the extractive rectification column (D2-2). At a point likewise above the feed of stream 17, preferably above the feed of stream 17, for example at the top of the column or downstream of the top condenser of the column, a stream 18 enriched in DMP, especially in 2,4-DMP, compared to stream 16 is withdrawn. Stream 18 preferably comprises a majority of the other compounds having a standard boiling point of 79 to 84° C., especially of 2,4-DMP, present in stream 16. Via a point below the feed of stream 16, preferably via the column bottom, a stream 19 comprising the extraction aid and cyclohexane is withdrawn, the cyclohexane/DMP concentration ratio, especially that of cyclohexane/2,4-DMP, being higher in stream 19 than in stream 16.

The extractive rectification column (D2-2) is preferably executed and operated in such a way that stream 18 comprises at most 100 ppm by weight, preferably at most 10 ppm by weight, more preferably at most 1 ppm by weight, of extraction aid. This can be achieved by virtue of the highest feed of an EHM-containing stream being at least 5, preferably at least 10, theoretical plates (as per the definition known to those skilled in the art) below the takeoff point of stream 18 and/or (D2-2) being operated with a reflux ratio of at least 5, preferably at least 10.

Stream 19, optionally after preheating, is conducted into the regeneration column (D2-3). From the regeneration column (D2-3), a stream 20 enriched in cyclohexane compared to stream 19 and a stream 21 depleted of cyclohexane compared to stream 19 (stream 21 comprises primarily the extraction aid, a portion of cyclohexane and any residual amount of other compounds having a standard boiling point of 79 to 84° C., especially of 2,4-DMP) are drawn off. From stream 21, a discharge stream (purge stream) 21 a is branched off, this making up preferably not more than 5%, more preferably not more than 1%, of the amount of stream 21. The remaining stream, optionally after cooling (which can also be effected in a thermally integrated system with a preheating of stream 19), is supplied at least partly to stream 17 and/or recycled into the extractive rectification column (D2-2) in the vicinity of stream 16.

Stream 20 comprises cyclohexane as the main constituent and can optionally be worked up further; for example, on-spec (high-purity) cyclohexane can be isolated from stream 20. Stream 20 can optionally also be combined with the cyclohexane or a cyclohexane-containing stream which is prepared in the process according to the invention in apparatus (IV) (according to step e)).

The invention claimed is:
1. A process for preparing cyclohexane, comprising the following steps:
 a) hydrogenating a hydrocarbon mixture (HM1), (HM1) comprising i) benzene, ii) methylcyclopentane (MCP), iii) dimethylpentanes (DMP), iv) possibly cyclohexane and v) possibly at least one compound selected from acyclic $C_5$-alkanes, cyclopentane and acyclic $C_6$-alkanes, to obtain a hydrocarbon mixture (HM2) having an elevated amount of cyclohexane compared to (HM1);
 b) feeding the hydrocarbon mixture (HM2) into a rectification column (D1);
 c) removing a stream (S1) comprising DMP and cyclohexane from the hydrocarbon mixture (HM2) via an outlet of the rectification column (D1), the outlet being below the feed to obtain the hydrocarbon mixture (HM2a) having a reduced amount of DMP compared to (HM2);
 d) optionally removing at least one compound selected from acyclic $C_5$-alkanes, cyclopentane and acyclic $C_6$-alkanes from the hydrocarbon mixture (HM2a) in a rectification column (D3) to obtain the hydrocarbon mixture (HM2b) having a reduced amount of at least one compound selected from acyclic $C_5$-alkanes, cyclopentane and acyclic $C_6$-alkanes compared to (HM2a);

e) isomerizing the hydrocarbon mixture (HM2a) or optionally the hydrocarbon mixture (HM2b) in the presence of a catalyst to obtain a hydrocarbon mixture (HM3) having an elevated amount of cyclohexane compared to (HM2a) or, if appropriate, compared to (HM2b); and f) isolating cyclohexane from the hydrocarbon mixture (HM3).

2. The process according to claim 1, wherein, in step c), the outlet of the rectification column (D1) is at the bottom of (D1).

3. The process according to claim 1, wherein, in step a), the hydrogenation of the hydrocarbon mixture (HM1) is performed in the presence of a catalyst comprising, as an active metal, at least one element of groups 8 to 10 of the Periodic Table of the Elements.

4. The process according to claim 1, wherein, in step a), the hydrogenation of the hydrocarbon mixture (HM1) is performed in the presence of a catalyst comprising, as an active metal, nickel or ruthenium.

5. The process according to claim 1, wherein the hydrocarbon mixture (HM2a) comprises at least 95% of the portion of MCP present in the hydrocarbon mixture (HM2), or the hydrocarbon mixture (HM2a) comprises at most 0.1% by weight (based on the total amount of MCP in (HM2a)) of DMP.

6. The process according to claim 1, wherein the hydrocarbon mixture (HM2a) comprises at least 98% of the portion of MCP present in the hydrocarbon mixture (HM2), or the hydrocarbon mixture (HM2a) comprises at most 0.02% by weight (based on the total amount of MCP in (HM2a)) of DMP.

7. The process according to claim 1, wherein the hydrocarbon mixture (HM2a) comprises at most 0.015% by weight (based on the total amount of MCP in (HM2a)) of 2,4-DMP.

8. The process according to claim 1, wherein, in step a), the hydrocarbon mixture (HM1)
  comprises cyclohexane as component iv) or
  comprises at least one compound selected from acyclic $C_5$-alkanes, cyclopentane and acyclic $C_6$-alkanes as component v),
  where, in the case that component b) is present in (HM1), step d) is necessarily conducted, and then, in step e), the hydrocarbon mixture (HM2b) is used rather than the hydrocarbon mixture (HM2a).

9. The process according to claim 1, wherein the catalyst used in step e) is an acidic ionic liquid comprising, as a cation, an at least partly alkylated ammonium ion or a heterocyclic cation or, as an anion, a chloroaluminate ion having the composition $Al_nCl_{(3n+1)}$ where $1<n<2.5$.

10. The process according to claim 1, wherein,
  i) in step f), cyclohexane is isolated in a purity of at least 98% by weight, or
  ii) step f) is performed in a rectification column (D4), by removing a stream (LB2) comprising MCP and possibly acyclic $C_5$-$C_6$-alkanes from the hydrocarbon mixture (HM3) in (D4) and fully or partly recycling stream (LB2) to step d) or to step e).

11. The process according to claim 1, wherein, in step f), cyclohexane is isolated in a purity of at least 99.5% by weight.

12. The process according to claim 1, wherein the hydrocarbon mixture (HM3) comprising cyclohexane, MCP, possibly acyclic $C_5$-$C_6$-alkanes and possibly higher-boiling components than cyclohexane is fed into a rectification column (D4), and the majority of the MCP and, if present, of acyclic $C_5$-$C_6$-alkanes present in the feed to (D4) is removed from (D4) at a withdrawal point above the feed.

13. The process according to claim 12, wherein the majority of the MCP and, if present, of acyclic $C_5$-$C_6$-alkanes present in the feed to (D4) is removed from (D4) via the top.

14. The process according to claim 10, wherein cyclohexane is drawn off from the rectification column (D4) in a purity of at least 98% by weight via the bottom of (D4) or via a side draw from (D4) below the feed.

15. The process according to claim 14, wherein cyclohexane is drawn off from the rectification column (D4) in a purity of at least 98% by weight via a vaporous side draw from (D4).

16. The process according to claim 14, wherein the cyclohexane-enriched stream drawn off via the bottom of (D4) is introduced into a rectification column (D5), and a stream (S5) comprising higher-boiling components than cyclohexane is removed via the bottom of (D5) and cyclohexane is drawn off with a purity of at least 98% by weight, via a takeoff point above the feed to (D5).

17. The process according to claim 16, wherein cyclohexane is drawn off with a purity of at least 99.5% by weight.

18. The process according to claim 16, wherein cyclohexane is drawn off via the top of (D5).

19. The process according to claim 14, wherein a cyclohexane-enriched stream is removed via the side draw from the rectification column (D4), the side draw being in the stripping section of (D4) or the cyclohexane-enriched stream from the side draw of (D4) being passed into an apparatus (D6) for further purification, in the form of a rectification column, and cyclohexane being obtained therein via a takeoff point above the feed of (D6) with a purity of at least 98% by weight.

20. The process according to claim 19, wherein cyclohexane is obtained via the top of (D6).

21. The process according to claim 19, wherein cyclohexane is obtained via a takeoff point above the feed of (D6) with a purity of at least 99.5%.

22. The process according to claim 10, wherein the rectification column (D4) takes the form of a dividing wall column, the dividing wall is partly above the feed point, a draw point is in the region of the dividing wall and this draw point is used to withdraw a liquid cyclohexane stream having a purity of at least 98% by weight.

23. The process according to claim 22, wherein the draw point is used to withdraw a liquid cyclohexane stream having a purity of at least 99.5% by weight.

24. The process according to claim 10, wherein stream (LB2) is recycled to step d), stream (LB2) being introduced into the hydrocarbon mixture (HM2a) upstream of the rectification column (D3) in which step d) is performed.

25. The process according to claim 1, wherein the stream (S1) removed from the hydrocarbon mixture (HM2) in step c) is introduced into a rectification apparatus (D2), cyclohexane being separated from DMP in (D2), and (D2) comprising an extractive rectification column or the cyclohexane-enriched stream drawn off from (D2) comprising at most 0.1% by weight.

26. The process according to claim 25, wherein the cyclohexane-enriched stream drawn off from (D2) comprises at most 0.015% by weight of 2,4-DMP.

27. The process according to claim 25, wherein the cyclohexane/DMP separation comprises the following steps i) to iii), the rectification apparatus (D2) being formed by the three components (D2-1) to (D2-3):

i) a rectification column (D2-1) in which the majority of the high boilers (based on the amount in the feed to (D2-1)) having a standard boiling point >84° C. is removed via the bottom and the majority of the cyclohexane and other compounds having a standard boiling point of 79 to 84° C. (based on the amount in the feed to D2-1) via the top, ii) an extractive rectification column (D2-2) in which the top product from (D2-1) is combined with an extraction aid and distilled in such a way that the majority of the extraction aid and of the cyclohexane are drawn off via the bottom and the majority of the other compounds having a standard boiling point of 79 to 84° C. present in the top product from (D2-1) are drawn off from (D2-2) via the top, and iii) a regeneration column (D2-3) in which the majority of the cyclohexane present in the bottom stream from (D2-2) is drawn off via the top and the majority of the extraction aid present in the bottom stream from (D2-2) via the bottom.

28. The process according to claim 25, wherein cyclohexane which originates from the rectification apparatus (D2) is combined with the cyclohexane which has been prepared in the isomerization in step e).

29. The process according to claim 1, wherein the hydrocarbon mixture (HM1) originates fully or partly from a steamcracking process.

* * * * *